United States Patent

Denis et al.

[11] Patent Number: 6,114,550
[45] Date of Patent: Sep. 5, 2000

[54] METHOD FOR THE STEREO-SELECTIVE PREPARATION OF A DERIVATIVE OF β-PHENYL-ISOSERINE AND ITS USE IN THE PREPARATION OF TAXANE DERIVATIVES

[75] Inventors: Jean-Noel Denis; Andrew-Elliot Greene, both of Uriage; Alice Kanazawa, Grenoble, all of France

[73] Assignee: Rhone-Poulenc Rorer S.A., Antony, France

[21] Appl. No.: 08/967,795

[22] Filed: Nov. 10, 1997

Related U.S. Application Data

[63] Continuation of application No. 08/411,693, filed as application No. PCT/FR93/00966, Oct. 4, 1993, Pat. No. 5,726,346.

[30] Foreign Application Priority Data

Oct. 5, 1992 [FR] France .................................. 92 11740

[51] Int. Cl.[7] .......................... C07D 305/14; C07C 51/06; C07C 229/08; C07C 271/00
[52] U.S. Cl. ............................. 549/510; 549/511; 560/27; 560/45; 562/406; 562/450
[58] Field of Search .................. 560/27, 45; 549/510, 549/511; 562/406, 450

[56] References Cited

U.S. PATENT DOCUMENTS 4,924,011  5/1990  Denis et al. ............................. 549/510
5,684,175  11/1997  Sisti et al. ................................. 560/27

FOREIGN PATENT DOCUMENTS 0 414 610   2/1991  European Pat. Off. .
WO 91/17976  11/1991  WIPO .
WO 91/17977  11/1991  WIPO .

OTHER PUBLICATIONS

McOmie J.F, "Protective Groups in Organic Chemistry", Plenum Press, pp. 98–100 (1973).
Greene et al., "Protective Groups in Organic Synthesis" (2d Ed.), John Wiley & Sons, Inc., pp. 10–53 and 410–420 (1991).

Primary Examiner—Ba K. Trinh
Attorney, Agent, or Firm—Finnegan, Henderson, Farabow, Garrett & Dunner, L.L.P.

[57] ABSTRACT

A β-phenylisoserine derivative of general formula (I):

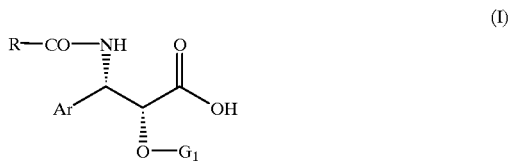

in the form of a salt or an ester, in which Ar represent an aryl radical, R represents a phenyl or naphthyl or a O—$R_1$ radical and $G_1$ represents —$CH_2$—Ph radical; and a method of using the same for making taxane derivatives.

6 Claims, No Drawings

METHOD FOR THE STEREO-SELECTIVE PREPARATION OF A DERIVATIVE OF β-PHENYL-ISOSERINE AND ITS USE IN THE PREPARATION OF TAXANE DERIVATIVES

This is a continuation of application Ser. No. 08/411,693 filed on Apr. 5, 1995 now U.S. Pat. No. 5,726,346, which is a 371 of PCT/FR93/00966 dated Oct. 4, 1993.

DESCRIPTION OF THE INVENTION

The present invention relates to a process for the stereo-selective preparation of a β-phenylisoserine derivative of general formula:

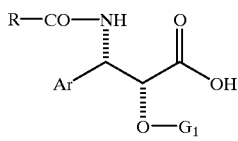

(I)

in which

Ar represents an aryl radical,

R represents a phenyl or α- or β-naphthyl radical optionally substituted with one or more identical or different atoms or radicals chosen from halogen atoms, alkyl radicals containing 1 to 4 carbon atoms and alkoxy radicals containing 1 to 4 carbon atoms, or a radical $R_1$—O in which $R_1$ represents:

an unbranched or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 11 carbon atoms, these radicals being optionally substituted with one or more substituents chosen from halogen atoms and hydroxyl radicals, alkyloxy radicals containing 1 to 4 carbon atoms, dialkylamino radicals in which each alkyl portion contains 1 to 4 carbon atoms, piperidino or morpholino radicals, 1-piperazinyl radicals (optionally substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl, cyano or carboxyl radicals or alkyloxycarbonyl radicals in which the alkyl portion contains 1 to 4 carbon atoms, or a phenyl radical optionally substituted with one or more atoms or radicals chosen from halogen atoms and alkyl radicals containing 1 to 4 carbon atoms or alkyloxy radicals containing 1 to 4 carbon atoms, or a saturated or unsaturated 4- or 6-membered nitrogenous heterocyclic radical optionally substituted with one or more alkyl radicals containing 1 to 4 carbon atoms, on the understanding that the cycloalkyl, cycloalkenyl or bicycloalkyl radicals can be optionally substituted with one or more alkyl radicals containing 1 to 4 carbon atoms, and $G_1$ represents a group protecting the hydroxyl function, chosen from methoxymethyl, 1-ethoxyethyl, benzyloxymethyl, 2,2,2-trichloroethoxymethyl, tetrahydrofuranyl, tetrahydropyranyl and β-(trimethylsilyl)ethoxymethyl radicals, trialkylsilyl radicals in which the alkyl radicals contain 1 to 4 arbon atoms, or —$CH_2$—Ph in which Ph represents a phenyl radical optionally substituted with one or more identical or different atoms or radicals chosen from halogen atoms, alkyl radicals containing 1 to 4 carbon atoms and alkoxy radicals containing 1 to 4 carbon atoms.

Preferably, Ar represents a phenyl or α- or β-naphthyl radical optionally substituted with one or more atoms or radicals chosen from halogen (fluorine, chlorine, bromine, iodine) atoms and alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, nitro and trifluoromethyl radicals, on the understanding that the alkyl radicals and alkyl portions of the other radicals contain 1 to 4 carbon atoms, that the alkenyl and alkynyl radicals contain 3 to 8 carbon atoms and that the aryl radicals are phenyl or α- or β-naphthyl radicals.

More especially, Ar represents a phenyl radical optionally substituted with one or more identical or different atoms or radicals chosen from halogen atoms and alkyl, alkoxy, amino, alkylamino, dialkylamino, acylamino, alkoxycarbonylamino and trifluoromethyl radicals.

Still more especially, Ar represents a phenyl radical optionally substituted with a chlorine or fluorine atom or with an alkyl (methyl), alkoxy (methoxy), dialkylamino (dimethylamino), acylamino (acetylamino) or alkoxycarbonylamino (tert-butoxycarbonylamino) radical.

Of even more special importance are the products of general formula (I) in which Ar represents a phenyl radical, R represents a phenyl or tert-butoxy radical and $G_1$ represents a benzyl or p-methoxybenzyl radical.

The products of general formula (I), and especially those for which $G_1$ represents —$CH_2$—Ph, which are new products constituting another subject of the present invention, are especially useful for preparing taxol or Taxotere and their analogues, by condensation with a baccatin III or 10-deacetylbaccatin III derivative in which the hydroxyl functions are suitably protected, working under the conditions described, for example, in European Patents EP 0,336,840 or EP 0,336,841.

It is known to prepare analogues of the product of general formula (I) from a β-phenylglycidic acid by working, for example, under the conditions described in European Patent EP 0,414,610.

It has now been found that the products of general formula (I) may be obtained directly, with very good enantio- and diastereoselectivity, by carrying out a process which requires far fewer steps to be carried out than according to the previously known processes.

According to the present invention, the products of general formula (I) may be obtained by the action of an N-carbonylarylimine of general formula:

in which Ar and R are defined as above, on the anion of an optically active amide of a protected hydroxyacetic acid, of general formula:

$$G_1-O-CH_2CO-\overset{*}{N}\begin{matrix}R_2\\R_3\end{matrix} \quad (III)$$

in which $G_1$ is defined as above and $$-\overset{*}{N}\begin{matrix}R_2\\R_3\end{matrix}$$

represents the residue of an optically active organic base, followed by hydrolysis of the product thereby obtained, of general formula:

$$R-CO-NH \quad O \\ \underset{Ar}{\overset{\vdots}{\rule{0pt}{1em}}} \overset{\vdots}{\underset{O-G_1}{\rule{0pt}{1em}}} \overset{*}{N}\begin{matrix}R_2\\R_3\end{matrix} \quad (IV)$$

in which R, Ar, $G_1$ and $$-\overset{*}{N}\begin{matrix}R_2\\R_3\end{matrix}$$

are defined as above.

It is especially advantageous to use an amide of general formula (III) in which $$-N\begin{matrix}R_2\\R_3\end{matrix}$$

represents an L(+)-2,10-camphorsultam residue of formula:

(V)

The process according to the invention is generally carried out by reacting the N-carbonyl-arylimine of general formula (II), optionally prepared in situ, with the previously anionized amide of the protected hydroxyacetic acid. The anionization is generally effected by means of an alkali metal amide. Amongst suitable amides, there may be mentioned sodium bis(trimethylsilyl)amide (NHMDS), lithium bis(trimethylsilyl)amide (LHMDS) or potassium bis (trimethylsilyl)amide (KHMDS), lithium diisopropylamide (LDA), lithium diethylamide (LDEA), lithium dicyclohexylamide (LDCHA), $(CH_3)_3SiN(R')Li$ (R'=alkyl, cycloalkyl, aryl) and tBuLi. Of very special importance is lithium bis(trimethylsilyl)amide which enables a high yield and excellent stereoselectivity to be obtained.

Generally, the anionization is performed in an inert organic solvent, for instance an ether such as tetrahydrofuran, at a temperature below 0° C. and preferably in the region of −78° C.

The action of the product of the general formula (II) on the previously anionized product of general formula (III) is generally performed in the same solvent and at the same temperature.

The product of general formula (IV) is hydrolysed to the product of general formula (I) by means of an inorganic base such as sodium hydroxide, potassium hydroxide or lithium hydroxide in an aqueous or aqueous-organic medium. It is especially advantageous to work in a tetrahydrofuran/water mixture in the presence of hydrogen peroxide. The reaction temperature is generally between −10 and 20° C., and preferably in the region of 0° C.

The N-carbonylarylimine of general formula (II) in which Ar is defined as above and R represents a t-butoxy radical is a new product which constitutes another subject of the present invention.

The N-carbonylarylimine of general formula (II) may be obtained by the action of an optionally substituted benzoyl halide or a reactive derivative of general formula:

$$R_1-O-CO-X \quad (VI)$$

in which $R_1$ is defined as above and X represents a halogen (fluorine, chlorine) atom or a residue $-O-R_1$ or $-O-CO-OR_1$, on a product of general formula:

$$Ar-CH=N-Z \quad (VII)$$

in which Ar is defined as above and Z represents a reactive group, for instance a trialkylsilyl radical such as a trimethylsilyl radical.

Generally, the action of the optionally substituted benzoyl halide or the product of general formula (VI) on the product of general formula (VII) is performed by heating in an organic solvent, for instance an ester such as ethyl acetate or a halogenated aliphatic hydrocarbon such as dichloromethane or chloroform or an aromatic hydrocarbon such as toluene or benzene.

The imine of general formula (VII) may be obtained from the aldehyde of general formula:

$$Ar-CHO \quad (VIII)$$

in which Ar is defined as above, according to known methods. For example, the product of general formula (VII) in which Z represents a trimethylsilyl radical may be obtained according to D. J. Hart et al., J. Org. Chem., 48, 289 (1983), by the action of lithium bis(trimethyldisilyl)amide (LHMDS), optionally prepared in situ by the action of butyllithium on bis(trimethylsilylamine), on the corresponding aldehyde of general formula (VIII).

The N-carbonylarylimine of general formula (II) may also be prepared in situ by the action of a strong base, for instance an amide such as lithium bis(trimethylsilyl)amide, on a thioether of general formula:

$$\underset{Ar}{\overset{S-C_6H_5}{\underset{NH-CO-R}{\rule{0pt}{1em}}}} \quad (IX)$$

in which Ar and R are defined as above.

The optically active amide of general formula (III) may be obtained by the action of an activated derivative of a protected hydroxyacetic acid of general formula:

  (X)

in which $G_1$ is defined as above, such as the halide or anhydride, on the optionally anionized corresponding chiral base.

The product of general formula (I) may be used to prepare the therapeutically active taxane derivatives of general formula:

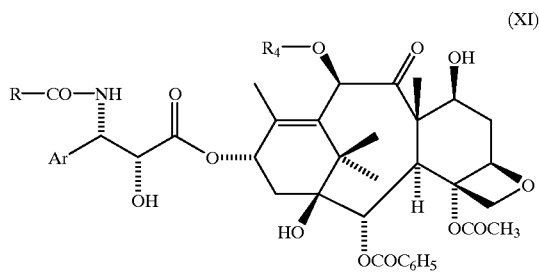

(XI)

in which Ar and R are defined as above and $R_4$ represents a hydrogen atom or an acetyl radical, in a process which consists in reacting a product of general formula (I) with a baccatin III or 10-deacetylbaccatin III derivative of general formula:

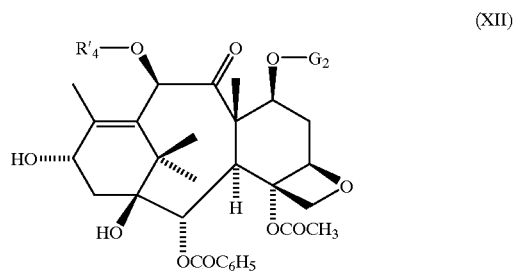

(XII)

in which $G_2$ represents a group protecting the hydroxyl function, such as a 2,2,2-trichloroethoxycarbonyl or trialkylsilyl radical, and $R'_4$ represents an acetyl radical or a group protecting the hydroxyl function, such as a 2,2,2-trichloroethoxycarbonyl radical, to obtain a product of general formula:

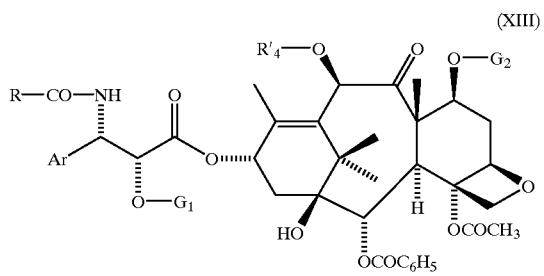

(XIII)

in which R, Ar, $G_1$, $G_2$ and $R'_4$ are defined as above, the protective groups $G_1$, $G_2$ and, where appropriate, $R'_4$ of which are replaced by hydrogen atoms, simultaneously or successively.

Generally, the esterification of a product of general formula (XII) with a product of general formula (I) is performed in the presence of a condensing agent, for instance a carbodiimide such as dicyclohexylcarbodiimide or a reactive carbonate such as 2-pyridyl carbonate, and an activating agent, for instance an aminopyridine such as 4-(dimethylamino)-pyridine or 4-pyrrolidinopyridine, working in an organic solvent such as an aromatic hydrocarbon (benzene, toluene, xylene, ethylbenzene, isopropylbenzene, chlorobenzene), an ether (tetrahydrofuran), a nitrile (acetonitrile) or an ester (ethyl acetate), at a temperature of between 0 and 90° C.

When $G_1$ represents a methoxymethyl, 1-ethoxyethyl, benzyloxymethyl, 2,2,2-trichloroethoxy-methyl, tetrahydrofuryl, tetrahydropyranyl or β-trimethylsilylethoxymethyl radical or a trialkylsilyl radical in which the alkyl radicals contain 1 to 4 carbon atoms, the replacement of the protective groups $G_1$, $G_2$ and, where appropriate, $R'_4$ of the product of general formula (XIII) is performed either with zinc, optionally in combination with copper, in the presence of acetic acid or by means of an inorganic or organic acid such as hydrochloric acid or acetic acid optionally dissolved in an aliphatic alcohol containing 1 to 3 carbon atoms, in the presence of zinc, optionally in combination with copper, when one of the protective groups represents a 2,2,2-trichloroethoxycarbonyl radical, or by treatment with an inorganic or organic acid such as hydrochloric acid or acetic acid optionally dissolved in an aliphatic alcohol containing 1 to 3 carbon atoms, when one of the protective groups represents a silyl radical.

When $G_1$ represents a —$CH_2$—Ph or, where appropriate, a benzyloxymethyl radical, the replacement of the protective groups $G_2$ and, where appropriate, $R'_4$ by hydrogen atoms is performed first, under the conditions described above, to obtain the product of general formula:

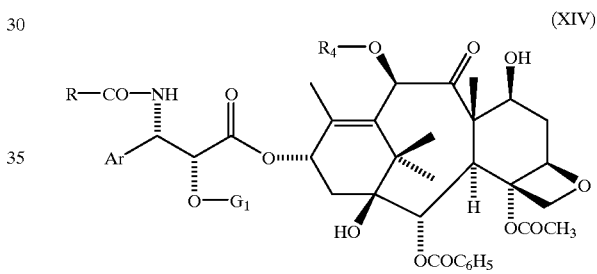

(XIV)

in which R, Ar and $R_4$ are defined as above, the Ph—$CH_2$— or, where appropriate, the benzyloxymethyl group of which is replaced by a hydrogen atom to obtain the product of general formula (XI).

The replacement of the Ph—$CH_2$— or, where appropriate, the benzyloxymethyl group of the product of general formula (XIV) by a hydrogen atom is generally performed by hydrogenolysis by means of hydrogen in the presence of a catalyst such as palladium black, working in an organic solvent such as acetic acid at a temperature of between 0 and 60° C., and preferably in the region of 40° C. It can be advantageous to work under pressure and optionally in the presence of a catalytic amount of an acid such as perchloric acid. The same replacement is also performed by the action of dichlorodicyanobenzoquinone (DDQ) in an organic solvent such as dichloromethane or acetonitrile.

The taxane derivatives of general formula (XI) thereby obtained may be optionally purified by application of the usual techniques.

EXAMPLES

The examples which follow illustrate the present invention.

Example 1

287 mg (0.79 mmol) of L-N-(benzyloxyacetyl)-2,10-camphorsultam and 3 cm³ of anhydrous tetrahydrofuran are introduced under an argon atmosphere into a 10-cm³ single-necked round-bottomed flask equipped with a magnetic stirrer system. The solution is cooled to −78° C., and 0.8 cm³ (0.8 mmol) of a 1M solution of lithium bis(trimethylsilyl) amide in tetrahydrofuran is then added dropwise. The mixture is left to react for 1 hour at −78° C., and 248 mg (1.21 mmol) of N-t-butoxycarbonylbenzylimine dissolved in 1.7 cm³ of anhydrous tetrahydrofuran are then added. After 15 minutes of reaction at −78° C., the reaction mixture is hydrolyzed by adding saturated aqueous ammonium chloride solution. It is extracted twice with dichloromethane. The combined organic phases are washed twice with water, then once with saturated aqueous sodium chloride solution and then dried over anhydrous magnesium sulphate. After filtration and removal of the solvents under reduced pressure, a residue (578 mg) is obtained, which is purified by chromatography on silica gel, eluting with a hexane/ethyl acetate mixture (85:15 by volume). 294 mg (0.52 mmol) of syn-L(+)-N-(2-benzyloxy-3-t-butoxycarbonylamino-3-phenylpropionyl)-2,10-camphorsultam, the characteristics of which are as follows, are thereby obtained in a 66% yield.

melting point: 79° C., then 130° C. (dichloromethane/hexane); optical rotation: $[\alpha]^{25}{}_D=+53°$ (c=0.98; chloroform) infrared spectrum (film): main characteristic absorption bands at 3450, 3050, 3020, 2975, 1720, 1500, 1460, 1420, 1395, 1370, 1340, 1280, 1240, 1220, 1170, 1140, 1100, 1070, 1020, 860, 810, 760, 750 and 700 cm⁻¹ proton NMR spectrum (300 MHz; CDCl₃; chemical shifts in ppm; coupling constants J in Hz): 0.99 (s, 3H); 1.1–1.6 (m, 2H); 1.28 (s, 3H); 1.39 (s, 9H); 1.83–2.25 (m, 5H); 3.51 ($AB_q$, $J_{AB}$=13.7, $\delta_A-\delta_B$=21.4, 2H); 3.94–4.03 (m, 1H); 4.36 ($AB_q$, $J_{AB}$=11.4, $\delta_A-\delta_B$=120, 2H); 4.86 (broad s, 1H); 5.33 (d, J=9.8, 1H); 5.60 (d, J=9.8, 1H); 6.9–7.05 (m, 2H); 7.14–7.4 (m, 8H). ¹³C NMR spectrum (75.47 MHz; CDCl₃): 19.97 (CH₃); 20.64 (CH₃); 26.59 (CH₂); 28.24 (CH₃); 32.81 (CH₂); 37.53 (CH₂); 44.49 (CH); 47.92 (C); 48.89 (C); 53.11 (CH₂); 55.70 (CH); 65.07 (CH); 72.47 (CH₂); 79.32 (C); 81.29 (CH); 126.78 (CH); 127.17 (CH); 127.65 (CH); 127.84 (CH); 128.09 (CH); 136.72 (C); 139.54 (C); 154.95 (C); 169.90 (C).

66 mg (0.116 mmol) of the product obtained above and 1 cm³ of a tetrahydrofuran/water mixture (4:1 by volume) are introduced under an argon atmosphere into a 10 cm³ single-necked round-bottomed flask equipped with a magnetic stirrer system. The mixture is cooled to 0° C., and 95 μl (0.93 mmol) of hydrogen peroxide containing 30% by volume and 20 mg (0.48 mmol) of hydrated lithium hydroxide (LiOH.H₂O) are then added. The mixture is left to react for 1 hour at 0° C. and then stirred for 15 hours at 20° C. A solution of 117 mg (0.93 mmol) of sodium sulphite in 0.7 cm³ of water is then added. After evaporation of the tetrahydrofuran, water is added, and the basic aqueous solution obtained is then extracted 3 times with dichloromethane. The basic aqueous phase is acidified to pH 1–2 by adding 2M aqueous hydrochloric acid solution, and is extracted 6 times with ethyl acetate. The combined organic phases are washed with saturated aqueous sodium chloride solution and then dried over anhydrous magnesium sulphate. After filtration and removal of the solvent under reduced pressure, 30 mg (0.081 mmol) of (2R,3S)-2-benzyloxy-3-t-butoxy-carbonylamino-3-phenylpropionic acid, the characteristics of which are as follows, are obtained in a 70% yield:

infrared spectrum (film): characteristic absorption bands at 3700–2300, 3450, 3300, 3075, 3050, 3025, 2975, 2925, 1720, 1660, 1510, 1500, 1450, 1390, 1370, 1250, 1165, 1110, 1020, 860, 740 and 695 cm⁻¹ proton NMR spectrum (200 MHz; CDCl₃; chemical shifts in ppm; coupling constants J in Hz): 1.42 (s, 9H); 4.20 (broad s, 1H); 4.52 ($AB_q$, $J_{AB}$=11.6, $\delta_A-\delta_B$=65, 2H); 5.30 (distorted d, J=9.9, 1H); 5.78 (distorted d, J=9.4, 1H); 6.2 (broad s, 1H); 7.0–7.06 (m, 2H); 7.06–7.44 (m, 8H) ¹³C NMR spectrum (50.3 MHz, CDCl₃): 28.24 (CH₃); 55.67 (CH); 72.90 (CH₂); 79.84 (CH); 80.49 (C); 126.60 (CH); 127.50 (CH); 127.95 (CH); 128.30 (CH); 136.40 (C); 139.36 (C); 155.66 (C); 173.08 (C). elemental analysis ($C_{21}H_{25}O_5N$)

| | | | | | | |
|---|---|---|---|---|---|---|
| calculated | C % | 67.91 | H % | 6.78 | N % | 3.77 |
| found | | 67.67 | | 6.68 | | 3.87 |

N-(t-Butoxycarbonyl)benzylimine may be prepared in the following manner:

20 cm³ (95 mmol) of freshly distilled bis(trimethylsilyl) amine are introduced under an argon atmosphere into a 100-cm³ single-necked round-bottomed flask equipped with a magnetic stirrer system, and then cooled to 0° C. 34 cm³ (85 mmol) of a 2.5M solution of n-butyllithium in hexane are then added dropwise. The temperature is allowed to rise to a value in the region of 20° C. and the mixture is then left to react for 10 minutes. It is cooled to 0° C., and 8.63 cm³ (85 mmol) of freshly distilled benzaldehyde are then added. The mixture is left to react at 0° C. for 3 hours 30 minutes. After removal of the solvent under reduced pressure, the residue is distilled under reduced pressure. 13.8 g (78 mmol) of N-(trimethylsilyl)benzylimine, the characteristics of which are as follows, are thereby obtained in a 92% yield:

infrared spectrum (film): main characteristic absorption bands at 3050, 3020, 2950, 2900, 2800, 2700, 1650, 1600, 1580, 1450, 1300, 1250, 1210, 1160, 1070, 1020, 970, 860, 840, 750 and 690 cm⁻¹ proton NMR spectrum (200 MHz; CDCl₃): 0.3 (s, 9H); 7.42–7.56 (m, 3H); 7.77–7.90 (m, 2H); 9.02 (s, 1H).

2.92 g (16.5 mmol) of the imine obtained above and then 50 cm³ of anhydrous chloroform are introduced under an argon atmosphere into a 100-cm³ single-necked round-bottomed flask equipped with a magnetic stirrer system. The mixture is cooled to 0° C., and 6.93 g (31.8 mmol) of pure di-t-butyl dicarbonate are then added dropwise. The reaction mixture is heated to reflux for 12 hours.

After removal of the chloroform under reduced pressure, the residue is distilled under reduced pressure (1.3 Pa) at 103–105° C. 1.91 g (9.3 mmol) of N-(t-butoxycarbonyl) benzylimine, the characteristics of which are as follows, are thereby obtained in a 56% yield:

infrared spectrum (film): 3050, 2970, 2925, 1730, 1650, 1605, 1590, 1485, 1460, 1320, 1275, 1260, 1220, 1155, 1000, 980, 885, 850, 755, 690 cm⁻¹ proton NMR spectrum (200 MHz, CDCl₃): 1.61 (s, 9H); 7.44–7.60 (m, 3H); 7.9–8.0 (m, 2H); 8.9 (s, 1H).

L-N-(Benzyloxyacetyl)-2,10-camphorsultam may be prepared in the following manner:

181 mg (0.84 mmol) of L(+)-10,2-bornanesultam dissolved in 2 cm³ of anhydrous toluene are introduced under an argon atmosphere into a 10-cm³ single-necked round-bottomed flask equipped with a magnetic stirrer system. The mixture is cooled to 0° C., and 50 mg (1.25 mmol) of 60% sodium hydride dispersed in mineral oil are then added. The mixture is left to react to 30 minutes at 0° C., and 0.17 cm³ (1.08 mmol) of benzyloxyacetyl chloride is then added. The temperature is allowed to rise to 20° C. and the mixture is then left to react for 2 hours. The reaction mixture is diluted by adding dichloromethane, and water is then added slowly.

The organic phase, separated after settling has taken place, is washed with water and then with saturated aqueous sodium chloride solution and finally dried over anhydrous magnesium sulphate. After filtration and removal of the solvents under reduced pressure, 511 mg of an oily residue are obtained, which residue is purified by chromatography on a column of silica gel, eluting with a hexane/ethyl acetate mixture (80:20 by volume). 294 mg (0.81 mmol) of L-N-(benzyloxyacetyl)-2,10-camphorsultam, the characteristics of which are as follows, are thereby obtained in a 97% yield:

infrared spectrum (film): main characteristic absorption bands at 2980, 2970, 1710, 1460, 1420, 1395, 1340, 1270, 1245, 1225, 1170, 1140, 1115, 1065, 1040, 1030, 985, 950, 870, 800, 780, 750 and 700 $cm^{-1}$ proton NMR spectrum (200 MHz; $CDCl_3$): 0.96 (s, 3H); 1.13 (s, 3H); 1.2–1.6 (m, 2H); 1.6–2.3 (m, 5H); 3.3–3.6 (m, 2H); 3.8–4.0 (m, 1H); 4.4–4.75 (m, 4H); 7.1–7.5 (m, 5H).

Example 2

42 mg (0.115 mmol) of L-N-(benzyloxyacetyl)-2,10-camphorsultam and 0.4 $cm^3$ of anhydrous tetrahydrofuran are introduced under an argon atmosphere into a 5-$cm^3$ single-necked round-bottomed flask equipped with a magnetic stirrer system. The mixture is cooled to −78° C., and 115 μl (0.115 mmol) of a 1M solution of lithium bis (trimethylsilyl)amide in tetrahydrofuran are then added. The mixture is left to react for 1 hour at −78° C., and 72 mg (0.23 mmol) of N-t-butoxycarbonyl-α-(phenylthio)benzylamine and 230 μl (0.23 mmol) of a 1M solution of lithium bis(trimethylsilyl)amide in tetrahydrofuran are then added. The reaction mixture is left to react for 1 hour 30 minutes at −78° C., and is then hydrolyzed by adding saturated aqueous ammonium chloride solution. The temperature is allowed to rise to 20° C. and the mixture is then extracted 3 times with ether. The combined organic phases are washed twice with water and then once with saturated aqueous sodium chloride solution and then dried over anhydrous magnesium sulphate. After filtration and removal of the solvents under reduced pressure, the residue obtained (114 mg) is purified by chromatography on a column of silica gel, eluting with a hexane/ethyl acetate mixture (85:15 by volume).

35 mg (0.062 mmol) of syn-L(+)-N-(2-benzyloxy-3-t-butoxycarbonylamino-3-phenylpropionyl)-2,10-camphorsultam, the characteristics of which are identical to those of the product obtained in Example 1, are thereby obtained in a 54% yield.

Example 3

94 mg (0.253 mmol) of (2R,3S)-2-benzyloxy-3-t-butoxycarbonylamino-3-phenylpropionic acid dissolved in 3.5 $cm^3$ of anhydrous toluene are introduced under an argon atmosphere into a 10-$cm^3$ single-necked round-bottomed flask equipped with a magnetic stirrer system. 52.3 mg (0.253 mmol) of distilled dicyclohexylcarbodiimide are then added. The mixture is left to react for 5 minutes at a temperature in the region of 20° C., and a mixture of 7.7 mg (0.063 mmol) of 4-(N,N-dimethylamino)pyridine and 56.3 mg (0.063 mmol) of 4-acetoxy-2α-benzoyloxy-5β,20-epoxy-1,13α-dihydroxy-9-oxo-7β,10β-bis(2,2,2-trichloroethoxycarbonyloxy)-11-taxene is then added all at once. The mixture is left to react for 20 hours at a temperature in the region of 20° C. The reaction mixture is diluted by adding 40 $cm^3$ of ethyl acetate. The organic phase is washed once with 5 $cm^3$ of distilled water, twice with 5 $cm^3$ of saturated aqueous sodium hydrogen carbonate solution and then once with 5 $cm^3$ of saturated aqueous sodium chloride solution and is finally dried over anhydrous sodium sulphate. After filtration and removal of the solvents under reduced pressure, a residue (166 mg) is obtained, which is purified by chromatography on a column of silica gel, eluting with an ether/dichloromethane mixture (1:99 by volume). 73 mg (0.0585 mmol) of 4-acetoxy-2α-benzoyloxy-5β,20-epoxy-1-hydroxy-9-oxo-7β,10β-bis(2,2,2-trichloroethoxycarbonyloxy)-11-taxen-13α-yl (2R,3S)-3-t-butoxycarbonylamino-3-phenyl-2-(benzyloxy)-propionate, the characteristics of which are as follows, are thereby obtained in a 93% yield:

optical rotation (repurified product) $[\alpha]^{25}_D$=−32° (c=0.86; chloroform) infrared spectrum (film): main characteristic absorption bands at 3450, 3050, 2970, 2920, 2900, 1760, 1740, 1720, 1600, 1580, 1490, 1450, 1375, 1242, 1175, 1165, 1100, 1060, 1000, 975, 960, 820, 770, 720 and 700 $cm^{-1}$ proton NMR spectrum (200 MHz; $CDCl_3$; chemical shifts in ppm; coupling constants J in Hz): 1.21 (s, 3H); 1.30 (s, 3H); 1.35 (s, 9H); 1.8–2 (m, 1H); 1.86 (s, 3H); 2.01 (s, 3H); 2–2.2 (m, 2H); 2.26 (s, 3H); 2.57–2.68 (m, 1H); 3.91 (d, J=7, 1H); 4.24 (s, 1H); 4.25 ($AB_q$, $J_{AB}$=8.7, $\delta_A-\delta_B$=43.8, 2H); 4.50 ($AB_q$, $J_{AB}$=12, $\delta_A-\delta_B$=109, 2H); 4.76 ($AB_q$, $J_{AB}$=11.8, $\delta_A-\delta_B$=91, 2H); 4.78 ($AB_q$, $J_{AB}$=12, $\delta_A-\delta_B$=7.6, 2H); 4.95 (distorted d, J=10.5, 1H); 5.14–5.36 (m, 1H); 5.4–5.6 (m, 1H); 5.57 (q, J=7.2 and 10.7, 1H); 5.71 (d, J=7, 1H); 6.2–6.33 (m, 1H); 6.26 (s, 1H); 7–7.1 (m, 2H aromatic); 7.22–7.86 (m, 11H aromatic); 8.06–8.11 (m, 2H aromatic). elemental analysis ($C_{56}H_{61}O_{18}NCl_6$)

| | | | | | | |
|---|---|---|---|---|---|---|
| calculated | C % | 53.86 | H % | 4.92 | N % | 1.12 |
| found | | 53.75 | | 5.15 | | 1.32 |

58 mg (0.0465 mmol) of the ester obtained above dissolved in 3 $cm^3$ of glacial acetic acid are introduced under an argon atmosphere into a 10-$cm^3$ single-necked round-bottomed flask equipped with a magnetic stirrer system. 3 $cm^3$ of methanol are then added, followed by 260 mg of zinc/copper system (prepared from 20 g of zinc and 3 g of copper sulphate monohydrate). The black heterogeneous medium is heated to 65° C. for 30 minutes. After cooling to a temperature in the region of 20° C., the reaction mixture is diluted in 40 $cm^3$ of ethyl acetate. It is filtered through Celite, and the solids are then washed 3 times with 20 $cm^3$ of ethyl acetate. The solvents are removed under reduced pressure. The residue obtained is purified by preparative thin-layer chromatography on silica gel, eluting with a methanol/dichloromethane mixture (5:95 by volume). 38 mg of 4-acetoxy-2α-benzoyloxy-5β,20-epoxy-1,7β,10β-trihydroxy-9-oxo-11-taxen-13α-yl (2R,3S)-3-t-butoxycarbonylamino-3-phenyl-2-(benzyloxy)propionate, the characteristics of which are as follows, are obtained in a 91% yield:

infrared spectrum (film): characteristic absorption bands at 3430, 3050, 2975, 2910, 2880, 1740, 1725, 1710, 1495, 1450, 1390, 1370, 1350, 1270, 1240, 1160, 1105, 1065 and 980 $cm^{-1}$ proton NMR spectrum (200 MHz; $CDCl_3$; chemical shifts in ppm; coupling constants J in Hz): 1.14 (s, 3H); 1.26 (s, 3H); 1.33 (s, 9H); 1.75 (s, 3H); 1.91 (s, 3H); 1.8–2.3 (m, 3H); 2.24 (s, 3H); 2.46–2.73 (m, 1); 3.91 (d, J=7, 1H); 4.12–4.38 (m, 3H); 4.20 (s, 1H); 4.51 ($AB_q$, $J_{AB}$=12, $\delta_A-\delta_B$=71, 2H); 4.94 (d, J=7.5, 1H); 5.21 (s, 1H); 5.13–5.29 (m, 1H); 5.44–5.6 (m, 1H); 5.69 (d, J=7, 1H); 6.27 (distorted t, J=7.3 and 8.8, 1H); 7–7.1 (m, 2H aromatic); 7.19–7.66 (m, 11H aromatic); 8.08–8.12 (m, 2H aromatic). elemental analysis ($C_{50}H_{59}O_{14}N$)

| calculated | C % | 66.87 | H % | 6.62 | N % | 1.56 |
| --- | --- | --- | --- | --- | --- | --- |
| found | | 66.65 | | 6.72 | | 1.73 |

14 mg (0.0156 mmol) of the product obtained above dissolved in 1.6 cm³ of glacial acetic acid are introduced under an argon atmosphere into 5-cm³ single-necked round-bottomed flask equipped with a magnetic stirrer system. 5 mg of palladium black are then added, and the mixture is thereafter placed under a hydrogen atmosphere. It is heated and stirred at 40° C. and then left to react for 6 hours. After cooling to a temperature in the region of 20° C., the reaction mixture is diluted in 5 cm³ of ethyl acetate. After filtration through Celite, the solids are washed with 5 times 5 cm³ of ethyl acetate. The combined organic phases are washed 3 times with 5 cm³ of saturated aqueous sodium hydrogen carbonate solution, 3 times with 5 cm³ of water and once with 5 cm³ of saturated aqueous sodium chloride solution and are then dried over anhydrous sodium sulphate. After filtration and removal of the solvents under reduced pressure, the residue obtained (14 mg) is purified by preparative thin-layer chromatography on silica, eluting with a methanol/dichloromethane mixture (5:95 by volume). 8.5 mg (0.0105 mmol) of 4-acetoxy-2α-benzoyloxy-5β,20-epoxy-1,7β,10β-trihydroxy-9-oxo-11-taxen-13α-yl (2R,3S)-3-t-butoxycarbonylamino-3-phenyl-2-hydroxypropionate (or Taxotere), the characteristics of which are identical to those described in the literature, are thereby obtained in a 67% yield.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What is claimed is:

1. A β-phenylisoserine derivative of general formula (I):

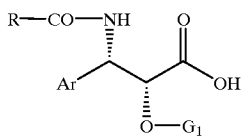

(I)

in the form of a salt or an ester, in which:

Ar represents an aryl radical;

R represents a phenyl or α- or β-naphthyl radical unsubstituted or substituted with one or more identical or different atoms or radicals selected from halogen atoms, alkyl radicals containing 1 to 4 carbon atoms, and alkoxy radicals containing 1 to 4 carbon atoms, or a radical $R_1$—O in which $R_1$ represents:

an unbranched or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 atoms, a cycloalkenyl radical containing 4 to 6 carbon atoms, or a bicycloalkyl radical containing 7 to 11 carbon atoms, these radicals unsubstituted or substituted with one or more substituents selected from halogen atoms, hydroxyl radicals, alkyloxy radicals containing 1 to 4 carbon atoms, dialkylamino radicals in which each alkyl portion contains 1 to 4 carbon atoms, piperidino radicals, morpholino radicals, 1-piperazinyl radicals (unsubstituted or substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl radicals, cyano radicals, carboxyl radicals, and alkoxycarbonyl radicals in which the alkyl portion contains 1 to 4 carbon atoms, wherein the cycloalkyl, cycloalkenyl, or bicycloalkyl radicals can be unsubstituted or substituted with one or more alkyl radicals containing 1 to 4 carbon atoms;

a phenyl or α- or β-naphthyl radical unsubstituted or substituted with one or more atoms or radicals selected from halogen atoms, alkyl radicals containing 1 to 4 carbon atoms, or alkyloxy radicals containing 1 to 4 carbon atoms; or a saturated or unsaturated 4- to 6-membered nitrogenous heterocyclic radical unsubstituted or substituted with one or more alkyl radicals containing 1 to 4 carbon atoms;

and $G_1$ represents a —$CH_2$—Ph radical in which Ph represents a phenyl radical unsubstituted or substituted with one or more identical or different atoms or radicals selected from halogen atoms and alkyl radicals containing 1 to 4 carbon atoms or alkoxy radicals containing 1 to 4 carbon atoms.

2. A method of using a compound of formula (I):

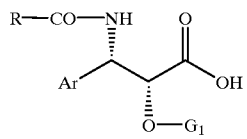

(I)

in the form of a salt or an ester, to prepare a compound of formula (XI):

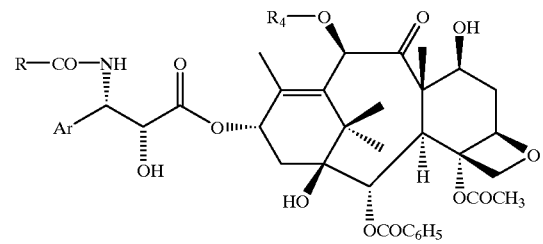

(XI)

wherein in formulae (I) and (XI):

Ar represents an aryl radical;

R represents a phenyl or α- or β-naphthyl radical unsubstituted or substituted with one or more identical or different atoms or radicals selected from halogen atoms, alkyl radicals containing 1 to 4 carbon atoms, and alkoxy radicals containing 1 to 4 carbon atoms, or a radical $R_1$—O in which $R_1$ represents:

an unbranched or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 atoms, a cycloalkenyl radical containing 4 to 6 carbon atoms, or a bicycloalkyl radical containing 7 to 11 carbon atoms, these radicals unsubstituted or substituted with one or more substituents selected from halogen atoms, hydroxyl radicals, alkyloxy radicals containing 1 to 4 carbon atoms, dialkylamino radicals in which each alkyl portion contains 1 to 4 carbon atoms, piperidino radicals, morpholino radicals, 1-piperazinyl radicals (unsubstituted or substituted at position 4 with an alkyl radical containing 1 to 4 carbon atoms or with a phenylalkyl radical in which the alkyl portion contains 1 to 4 carbon atoms), cycloalkyl radicals containing 3 to 6 carbon atoms, cycloalkenyl radicals containing 4 to 6 carbon atoms, phenyl radicals, cyano radicals, carboxyl radicals, and alkoxycarbonyl radicals in which the alkyl portion contains 1 to 4 carbon atoms, wherein the cycloalkyl, cycloalkenyl, or bicycloalkyl radicals can be unsubstituted or substituted with one or more alkyl radicals containing 1 to 4 carbon atoms;

a phenyl or α- or β-naphthyl radical unsubstituted or substituted with one or more atoms or radicals selected from halogen atoms, alkyl radicals containing 1 to 4 carbon atoms, or alkyloxy radicals containing 1 to 4 carbon atoms; or a saturated or unsaturated 4- to 6-membered nitrogenous heterocyclic radical unsubstituted or substituted with one or more alkyl radicals containing 1 to 4 carbon atoms;

$G_1$ represents a —CH$_2$—Ph radical in which Ph represents a phenyl radical unsubstituted or substituted with one or more identical or different atoms or radicals selected from halogen atoms, alkyl radicals containing 1 to 4 carbon atoms, or alkoxy radicals containing 1 to 4 carbon atoms; and $R_4$ represents a hydrogen atom or an acetyl radical;

the process comprising:

a) reacting the product of formula (I) with a baccatin III or 10-deacetylbaccatin III derivative of formula (XII):

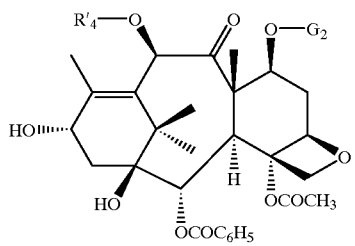

(XII)

to obtain a compound of formula (XIII):

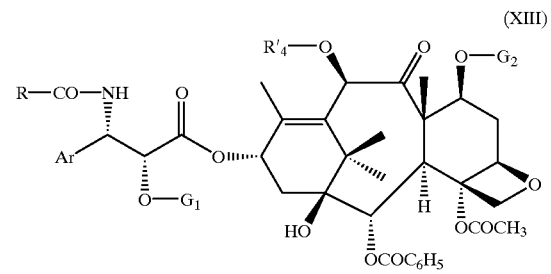

(XIII)

wherein in formulae (XII) and (XIII):
Ar, R, and $G_1$ are defined as above;
$G_2$ represents a 2,2,2-trichloroethoxycarbonyl radical or a trialkylsilyl radical; and
$R'_4$ represents an acetyl radical or a 2,2,2-trichloroethoxycarbonyl radical;

(b) replacing $G_2$ and, where appropriate, $R'_4$ with hydrogen atoms to obtain a compound of formula (XIV):

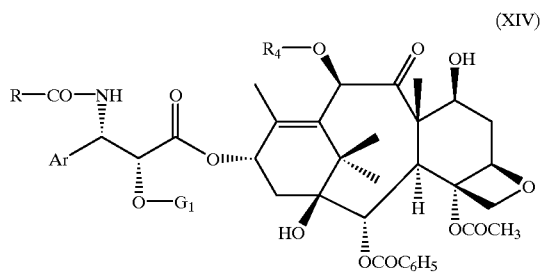

(XIV)

wherein Ar, R, and $G_1$ are defined as above and $R_4$ represents an acetyl radical or a hydrogen atom; and (c) replacing $G_1$ with a hydrogen atom to obtain the formula (XI) compound.

3. The method according to claim 2, wherein step (a) is performed in the presence of a condensing agent or a reactive carbonate and an activating agent in an organic solvent selected from aromatic hydrocarbons, ethers, nitrites, and esters at a temperature between 0 and 90° C.

4. The method according to claim 2, wherein step (b) is performed with zinc, optionally in combination with copper, in the presence of acetic acid or an inorganic or organic acid dissolved in an aliphatic alcohol when $G_2$ and/or $R'_4$ represent a 2,2,2-trichloroethoxycarbonyl radical, or by treatment in an acid medium when $G_2$ represents a trialkylsilyl radical.

5. The method according to claim 2, wherein step (c) is performed by hydrogenolysis.

6. The method according to claim 5, wherein the hydrogenolysis is performed by means of hydrogen in the presence of a catalyst or by action of dichlorodicyanobenzoquinone in an organic solvent.

* * * * *